(12) United States Patent
Respini et al.

(10) Patent No.: US 9,377,450 B2
(45) Date of Patent: Jun. 28, 2016

(54) PROCESS FOR PREDICTING THE STABILITY OF CRUDE OIL AND EMPLOYING SAME IN TRANSPORTING AND/OR REFINING THE CRUDE OIL

(71) Applicant: BAKER HUGHES INCORPORATED, Houston, TX (US)

(72) Inventors: Marco Respini, Casalmorano (IT); Giuseppe Della Sala, Liverpool (GB); Gavin M. Medine, Amsterdam (NL); Corina L. Sandu, Pearland, TX (US); Sai Reddy Pinappu, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 210 days.

(21) Appl. No.: 13/924,089

(22) Filed: Jun. 21, 2013

(65) Prior Publication Data

US 2013/0341241 A1 Dec. 26, 2013

Related U.S. Application Data

(60) Provisional application No. 61/663,441, filed on Jun. 22, 2012.

(51) Int. Cl.
| | |
|---|---|
| *C10G 75/00* | (2006.01) |
| *G01N 33/28* | (2006.01) |
| *G01N 21/41* | (2006.01) |
| *G01N 21/85* | (2006.01) |
| *G01N 21/84* | (2006.01) |

(52) U.S. Cl.
CPC .............. *G01N 33/2835* (2013.01); *C10G 75/00* (2013.01); *G01N 21/41* (2013.01); *G01N 21/8507* (2013.01); *G01N 2021/8416* (2013.01); *Y10T 137/0324* (2015.04)

(58) Field of Classification Search
CPC .............. G01N 33/2835; G01N 21/41; G01N 2021/8416; G01N 21/8507; C10G 75/00
See application file for complete search history.

(56) References Cited

U.S. PATENT DOCUMENTS

| | | | |
|---|---|---|---|
| 5,871,634 A | 2/1999 | Wiehe et al. | |
| 5,997,723 A | 12/1999 | Wiehe et al. | |
| 8,236,564 B2* | 8/2012 | Pauli et al. | ...................... 436/29 |
| 2002/0140925 A1* | 10/2002 | Mougin | .......................... 356/70 |
| 2010/0163461 A1* | 7/2010 | Wright et al. | ............ 208/48 AA |
| 2012/0125087 A1* | 5/2012 | Sandu et al. | .................. 73/64.55 |

OTHER PUBLICATIONS

ASTM D7157-12 Standard Method for Determination of Intrinsic Stability of Asphaltene-Containing Residues, Heavy Fuel oils, and crude oils.*

Andersen, S., "Flocculation Onset Titration of Petroleum Asphaltenes," Energy and Fuels, 1999, vol. 13, pp. 315-322.

(Continued)

*Primary Examiner* — Randy Boyer
*Assistant Examiner* — Juan Valencia
(74) *Attorney, Agent, or Firm* — Mossman, Kumar & Tyler, P.C.

(57) ABSTRACT

A process for refining crude oil can be controlled to mitigate fouling by deploying a refractive index probe at a location suitable for making a crude oil stability determination, wherein the crude oil stability determination is relevant to controlling the refining process; making a measurement of crude oil stability; and then controlling the process for refining crude oil by maintaining the process or implementing a change to the process, based upon the determination of crude oil stability. This concept can also be applied to transporting, blending, and storing crude oil.

14 Claims, 1 Drawing Sheet

(56) References Cited

OTHER PUBLICATIONS

Buckley, J.S. et al., "Asphaltene Precipitation and SOlvent Properties of Crude Oils," Petroleum Science and Technology, 1998, vol. 16 (3&4), pp. 251-285.

ASTM Designation D7157-12: Standard Test Method for Determination of Intrinsic Stability of Asphaltene—Containing Residues, Heavy Fuel Oils and Crude Oils (n-Heptane Phase Separation; Optical Detection.

* cited by examiner

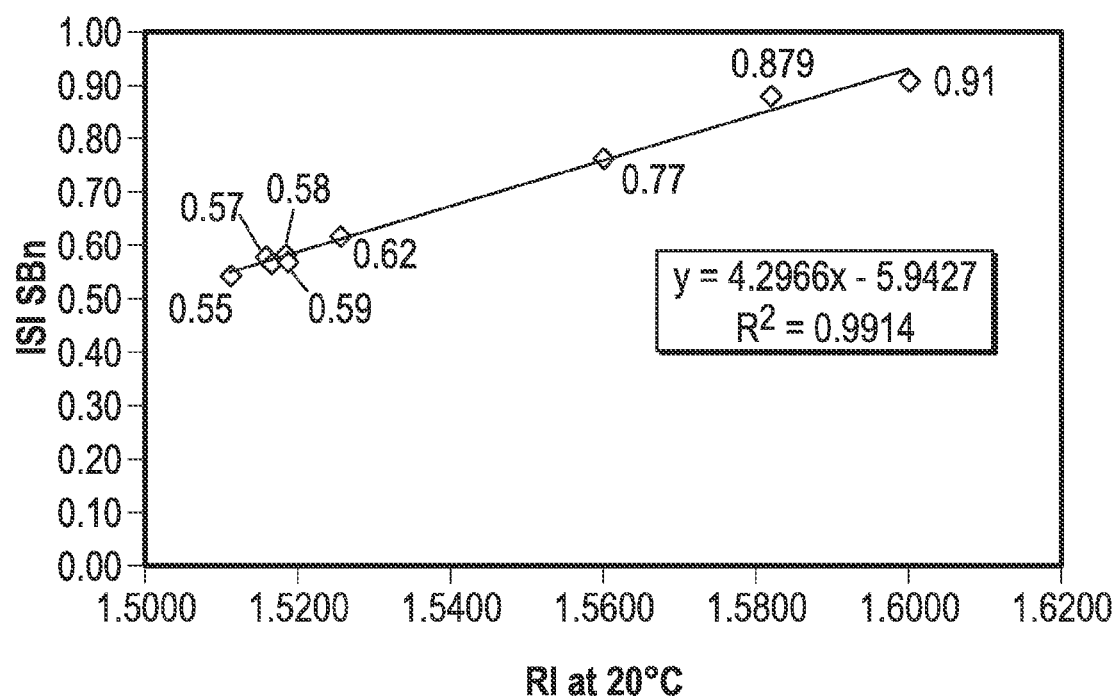

PROCESS FOR PREDICTING THE STABILITY OF CRUDE OIL AND EMPLOYING SAME IN TRANSPORTING AND/OR REFINING THE CRUDE OIL

CROSS REFERENCE TO RELATED APPLICATIONS

This patent application claims priority from the U.S. Provisional Patent Application having the Ser. No. 61/663,441 which was filed on Jun. 22, 2012 and which application is hereby incorporated by reference in its entirety.

BACKGROUND OF THE APPLICATION

1. Field of the Invention

This invention relates to transporting, storing, blending, and refining crude oil. This invention particularly relates to using online instruments to monitor and/or control transporting, storing, blending, and refining crude oil.

2. Background of the Prior Art

As world reserves of light, sweet crudes diminish and worldwide consumption of oil increases, refiners seek methods for extracting useful products such as gasoline and fuel oils from heavier crude resources. While not as desirable and easy to process, extensive reserves in the form of "heavy crudes" exist in a number of countries, including Western Canada, Venezuela, Russia, the United States, and elsewhere.

For example, heavy or extra heavy crude oil can be found in the Orinoco Belt in Venezuela, the oil sands in Canada, and the Ugnu Reservoir in Northern Alaska. Alberta produces approximately two-thirds of Canada's oil and more than three-quarters of its natural gas. Nearly half of Alberta's oil is mined from vast oil sands, which contain deposits of a heavy crude oil called bitumen. Alberta's oil sands represent the largest known deposits of bitumen in the world. The oil sands occur in three major areas of the province: the Athabasca River Valley in the northeast, the Peace River area in the north, and the Cold Lake region in east central Alberta.

Such heavy oils (even some not so heavy oils) are often difficult to refine because of their viscosity and propensity for being unstable and precipitating solids upon storage and processing, most notable asphaltenes. Asphaltenes are high molecular weight aromatic carbonaceous compositions, normally solid at room temperature. When they precipitate from crude oil, they can foul equipment and reduce the quality of the products being refined. Other issues associated with heavy crude oil include: high solids; increased amounts of entrained water; and high sulfur content; high total acid number (TAN) and high metals. Asphaltene deposition is a well-known problem affecting all aspects of petroleum production and processing. Crude oils containing high or low levels of asphaltenes can be destabilized while processing causing fouling, formation of sludge, corrosion and all the equipment fixing, cleaning, and cost aggravations associated with these effects.

Additional operational problems observed with heavy crude oil: difficulty in blending crude streams, increased unit upsets, increased pollution, loss of through-put, difficulty with desalting, increased load on wastewater plants, increase in air emissions, and flexibility in plant operations is reduced. All of this leads to an overall increase in operating costs. It follows that it would be desirable in the art to be able to use an online method of monitoring and predicting the stability of crude oil so that the crude oil could be more efficiently stored, transported, blended, and refined.

SUMMARY OF THE INVENTION

In one aspect, the invention is a method for controlling a process for refining crude oil to mitigate fouling comprising: deploying a refractive index probe at a location suitable for making a crude oil stability determination, wherein the crude oil stability determination is relevant to controlling the refining process; making a measurement of crude oil stability; and then controlling the process for refining crude oil by maintaining the process or implementing a change to the process, based upon the determination of crude oil stability.

In another aspect, the invention is a method of transporting or storing crude oil to mitigate fouling comprising: deploying a refractive index probe in a crude oil transportation or storage system; making a measurement of crude oil stability; and then controlling the process for transporting or storing the crude oil by maintaining the process or implementing a change to the process, based upon the determination of crude oil stability.

In still another aspect, the invention is a method of monitoring the blending of two or more crude oil streams to form a combined feed stream to identify their stability and compatibility as well as to avoid inducing fouling comprising employing a refractive index probe to measure at least the stability of the combined streams.

Another aspect, the invention is a method of monitoring the blending of two or more crude oil streams to form a combined feed stream to identify their stability and compatibility as well as to avoid inducing fouling comprising employing a refractive index probe to measure at least the stability of the feed streams used to prepare the combined streams. In this aspect, the use of the refractive index probe to determine the blending order may also be determined.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIG. 1 is an exemplary correlation between refractive index and $SB_n$ of a crude oil.

DETAILED DESCRIPTION OF THE INVENTION

For the purposes of the application, the term "unstable" when used regarding crude oil means that the subject crude oil has undesirable properties generally not immediately apparent, but that develop over time both during and after storage. The precipitation of asphaltenes from crude oil is an example of such instability. Asphaltenes are generally considered to be the highest molecular weight and most polar component of a crude oil. They are viewed as colloidal dispersions of solids in a nonaqueous solvent. When separated from an oil, asphaltenes are dark brown to black solids.

By definition, asphaltenes are a solubility class. Asphaltenes are present in the fraction of a petroleum fluid or bitumen that is insoluble in heptane and soluble in benzene or toluene. More specifically, asphaltenes are the fraction separated from petroleum by the addition of a minimum of forty volumes of a solvent having a surface tension lower than 25 dynes $cm^{-1}$.

In one aspect, the invention is a method for refining crude oil comprising deploying a refractive index (sometimes abbreviated herein as RI) probe at a location suitable for making a crude oil stability determination, wherein the crude oil stability determination is relevant to controlling the refining process; making a measurement of crude oil stability; and then controlling the process for refining crude oil by maintaining the process or implementing a change to the process, based upon the determination of crude oil stability. In the practice of method of the Application, the determination of crude oil stability may have two parts. The first part is measuring RI parameters online using a refractive index probe. The RI values generated will be converted to a "solubility blending number" ($SB_n$) based on a linear correlation. The linear correlation may be established using any method known to the art, such as, for example, that disclosed in the method published by the New Mexico Petroleum Recovery Research Center as PRRC 01-18. This document, authored by Jianxin Wang and Jill Buckley and having the title: *Procedure for Measuring the Onset of Asphaltenes Flocculation*. Using this procedure, a linear correlation between the solubility parameter, δ, and FRI at 20° C. may be established:

$$\delta = 52.042 F_{RI} + 2.904 \quad (2)$$

where δ is in units of $MPa^{0.5}$ and $F_{RI}$ is $(RI^2-1)/(RI^2+2)$.

This correlation was established based on the one-third rule that relates that the function of the refractive index divided by the mass density is a constant equal to ⅓ for all different compounds. This rule was validated on more than 229 crude oils at 20° C. as well as higher temperatures up to 80° C.

In addition to this method of establishing an $SB_n$ based on the existing correlations from prior art referenced above, the $SB_n$ is also periodically determined using a turbidimetric flocculation titration method as a check on accuracy. In one embodiment of the method of the disclosure, this determination may be made using Baker Hughes Field ASIT services technology. A triple dilution approach is typically involved. The Field ASIT services technology allows measuring the ASI values for the intrinsic sample (undiluted) as well as for the diluted samples. Field ASIT technology is an optical method using a coherent light source that allows measuring the transmittance through the sample and relates especially to measuring the onset flocculation of asphaltenes within a crude sample. Changes in the sample transmittance (such as asphaltene aggregation and precipitation) are induced via temperature and/or via adding a solvent such as n-alkane (pentane, heptane, dodecane). The transmittance changes versus temperature or solvent addition are measured with high degree of sensitivity and repeatability. From these measurements a proprietary index calculation is performed, namely Asphaltene Stability Index (ASI) that allows one to describe sample stability with respect to asphaltenes. To determine solubility blending number, SBn for a sample a three dilution approach is used. Crude sample of known amounts are diluted at three different ratios: 1:1, 1:2 and 1:1.5 typically. By plotting the ASI on the y-axis and dilution ratio on x-axis one can obtain a linear correlation. From this SBn values (intercept on the y-axis) as well as In values (the slope) can be derived. $I_n$ stands for the insolubility number of the asphaltenes within the crude sample and is related to the asphaltene peptizability parameter via the following relation (Pa=1−In). ASI values are calculated based on these parameters. Other methods of performing this analysis may be employed. Any turbidimetric flocculation titration method known to those of ordinary skill in the art may be employed with the methods of the application.

FIG. 1 shows an exemplary correlation between a refractive index and the $SB_n$ for crude oil at 20° C. This correlation was prepared by first testing crude oil samples using a refractive index probe and a near IR spectrophotometer as disclosed in US-A-20120125087A1, which reference is incorporated herein by reference in its entirety.

The $SB_n$ values for each sample was then determined using the method disclosed in U.S. Pat. No. 5,871,634, which is incorporated by reference in its entirety. As already noted, this method includes adding a non-solvent to crude oil and determining the onset flocculation of asphaltenes. It is routine to make at least 3 measurements requiring from 60 minutes to two hours to dependably make an $SB_n$ determination using this method. This delay has in the past precluded the use of $SB_n$ as a real time measurement for control of a refining or transportation and storage process. In addition, there is another limiting component. The viscosity of some sample is too low such as it will require much larger ratios to allow the operator to measure it. The linearity correlation usually very valid at low sample/solvent ratios can be significantly altered at higher solvent/sample ratios such will make difficult to obtain an accurate SBn value.

Thus, this invention introduces another method of correcting for larger contribution effects via RI measurements. It is proposed to use online RI measurements and obtain the SBn values for the analyzed feed. Knowing the SBn of the crude of interest from RI measurements it is proposed to customize the solvent of choice to mimic the SBn values of the crude such to introduce minimum effect due to solvent addition. In this way elimination of the 3-dilution approach (less time consuming) is introduced and accurate determination of both In as well as SBn is obtainable.

The ASI value may be employed to determine whether a particular stream may be transported, blended, stored or refined. Since no system is exactly alike, the operator of any refinery or pipeline or storage facility will well know what values of the ASI are acceptable for their equipment and systems. Variables in these systems include, for pipe lines and storage facilities, pipe diameter, stream temperature, stream velocity and the availability and type of agitation or stirring present, if any. For a refining unit, variables which influence the stability required in the crude oil used to feed the plant include the ability to heat the process streams and residence time inside of reactors, reformers, cokers and other types of refinery equipment.

If a feed is within specification for ASI, then the operator may elect to do nothing in a refinery. Often though, it may be desirable to make some change to a process or blending crudes or crude mixing order or adding chemical solutions to prevent fouling or other problems associated with feeding unstable crude oil unless the ASI is within specification or even if it is just not at an optimum level. In one embodiment of the method of the application, the operator may elect to change operating parameters including, but not limited to changing fluid flow velocities, changing unit operating temperatures, changing unit residence times, and the like.

In another embodiment, the operator may elect to make changes by mixing at least two feed streams, to bring the ASI of the combined stream within specification for the refining unit of interest, thus optimizing the SBn of both streams. In some embodiments, the second feed stream may not even be crude oil. For example, a refinery may elect to use a lighter feed stock such as gail oil, paraffinic feed, lighter cuttur stocks, etc. that could be recovered and recycled.

In yet another embodiment, the mixing or blending of feed streams may be the blending of streams that are often prone to problems. One such is the blending of heavy crude oil and shale oil. Shale oil is paraffinic and is often prone to blending problems.

In combining or blending feed streams, any method of performing this function may be employed. For example, the feed streams may be introduced into a tank and agitated. In an alternative embodiment, the feed streams may be co-injected into a line having static mixers in place. In still another embodiment, both methods may be employed to mix crude oil feed streams to prepare a crude oil feed stream.

In those embodiments of the method of the Application where the ASI is not within specification, remedial efforts may be employed to mitigate the instability of the crude oil. At least one such remedial effort may be to use a stabilizing additive. Any additive known to be useful to those of ordinary skill in the art may be employed with the method of the application. For example, in one embodiment, the additive is prepared from a formulation including: a first component selected from the group consisting of (alkoxylated)-(di or tri)-alkyl phenol—aldehyde (amine) resins; α-Olefin—maleic anhydride co-polymers and grafted polymers including half ester/amide and full ester/amide derivatives; and combinations thereof. Such a formulation may also include a second component which is a synergist and selected from the group consisting of polyamines, amidoamines, imidazolines, and combinations thereof.

The additives useful with the methods of the application may function to increase the stability of the crude oil. In such embodiments, the additives are often employed at a concentration from about 0.025 to about 10 wt %.

Embodiments of the methods of the application may be employed in any application where crude oil is being transported, moved or processed and it would be desirable to avoid destabilization of the crude oil after transportation and storage, and/or processing because once precipitation of the asphaltenes and aggregation is formed too much energy and cost will be needed to redisperse them, and sometimes redispersion is nearly impossible.

By combining the use of an RI probe to determine $SB_n$ and turbidimetric flocculation titrations to correlate the $SB_n$ for the subject stream with the ASI, the method of the application avoids the distortion to $SB_n$ caused by employing solvents to precipitate asphaltenes or depending exclusively upon the RI measurements. Depending upon the crude oil involved, it is sometimes difficult to nearly impossible to accurately determine the $SB_n$ using one or the other of these methods. A resultant error in the ASI can cause severe fouling which in turn can cause costly downtime, and in severe circumstances, unit turnarounds.

As already stated above, employing the Field ASIT services technology or other such multiple dilution titration method is time consuming. One advantage of the method of the application is that generally this time-consuming titration need only be performed periodically, sometimes as infrequently as once per "batch" of crude oil. Of course, in some embodiments wherein large batches of crude oil are being transported or stored or blended, it may be desirable to run this test more frequently. Generally speaking though, once it has been determined that the RI method is accurate and/or a correction has been applied, there does not tend to be a change in the ASI value absent a substantial change to the conditions are quality of the crude oil.

It follows then, that in some embodiments of practicing the methods of the application, after first ascertaining the ASI value, the operator will monitor the ASI using only the RI data in order to prevent an unexpected change to the conditions or the quality of the crude oil.

In practicing the methods of the application, a refractive index probe is deployed at a location suitable for making a crude oil stability determination, wherein the crude oil stability determination is relevant to controlling the refining process. In one embodiment, it may be desirable to place a RI probe into the feed going into a desalting unit. As crude oil comes into the refinery tankage, it generally contains sand, minerals, and salts plus iron oxides that have flaked off equipment during transportation. All of these may cause fouling during the refining process.

Much of this material will settle out in the crude oil tanks, but the salt is mostly in tiny droplets of water dispersed throughout the crude oil. Much of this water will not drop out with just settling, so desalting is carried out in desalting units. Some of these units function by adding fresh water to the crude. In many cases, the water will dissolve almost all the salt and then drop to the bottom of the desalter for removal. In other, more stubborn situations, the crude oil is passed through a high voltage electrical field that is sometimes as high as 12,000 to 35,000 volts. That causes the tiny, salt laden water droplets to coalesce and then settle out.

When going through a desalter, crude oil may be subjected to a change in temperature. In some instances, this is sufficient to destabilize crude oil. By placing an RI probe at this point of a refinery process, an operator could be warned of the onset of fouling and it could then take mitigating steps. In one embodiment of a method of the application, the operator may elect to add an additional feed stream to the desalter wherein the additional feed stream would stabilize the first feed stream. In an alternative embodiment, the operator may elect to employ an additive; select a demulsifier with a different charge; or change the temperature or water feed rate of the desalting unit.

Upstream of a desalting unit in most refineries is a heat exchanger often called a cold train. In some embodiments of the method of the application, it may be desirable to place an RI probe at this location. With a probe in this location, an operator would have the option to mitigate fouling by increasing temperatures, employing additives, or increasing the sheer forces on the crude oil as it passes through the exchanger.

Yet another location for an RI probe would be the preheater located between the desalter and first furnace. To mitigate fouling downstream, the operator would, in most embodiments, adjust the temperature of the pre-heater or employ additives. The method of the application may be practiced by employing RI probes at any location within a refinery where a determination of $SB_n$ could be useful in mitigating fouling.

In methods of the application related to the storage and transportation of crude oil, it may be desirable to employ an RI probe in a sample loop or directly in a crude oil storage tank. To mitigate fouling, an operator having a probe in this location may elect to feed more stable crude oil, increase agitation and/or stirring, or employ additives.

Another embodiment of the method of the application is the use of RI determined ASI values in the blending of different crude oils to generate batches of the feed streams. For example, the method of the application may be employed to determine ASI values for the crude oils entering into a storage vessel in order to properly ratio the feed rates of the crude oils to produce a batch of crude oil to use as a feed stream for a refinery. In another embodiment, the method of the application may be employed to monitor homogenization of the contents of the crude oil storage vessel by observing the changes in ASI therein.

EXAMPLES

The following examples are provided to illustrate the present invention. The examples are not intended to limit the scope of the present invention and they should not be so interpreted. Amounts are in w/v parts or w/v percentages unless otherwise indicated.

Hypothetical Example 1

A sample of a crude oil feed stream is tested to determine its ASI value using both a refractive index probe and ASIT technology. The operator of a desalter and refinery determines that the crude oil is too unstable to be sent through the desalting unit. The feed stream is diverted to a storage vessel and treated with an additive to mitigate its instability. The treated crude oil feed stream is then sent through the desalter and produces only nominal fouling.

Hypothetical Example 2

A sample of a crude oil within a storage vessel is tested to determine its ASI value using both a refractive index probe and ASIT technology. It is determined that the crude all resident therein is too unstable to be refined without causing significant fouling. Sufficient light crude is charged to the storage vessel to render the crude oil batch resulting therefrom sufficiently stable for refining.

Hypothetical Example 3

An operator at a refinery notes that the ASI number for a crude oil feed to a cold train is deteriorating. The operator investigates the cause and determines that there is a malfunction in the cold train resulting in a too long residence therein. The operator overrides the defective device causing the problem thereby avoiding excess of fouling in the desalter downstream from the cold train.

What is claimed is:

1. A method for controlling a process for refining crude oil to mitigate asphaltene fouling comprising:
    deploying a refractive index probe at a location suitable for making a crude oil stability determination, wherein the location is selected from the group consisting of: into a feed going into a desalting unit, into a heat exchanger, into a pre-heater, and combinations thereof;
    making a measurement of crude oil stability by a process comprising:
        a first part of measuring RI parameters online using the refractive index probe; and
        a second part of the process of converting the RI parameters into a "solubility blending number" ($SB_n$) based on a linear correlation; and
    then controlling the process for refining crude oil using the $SB_n$ by maintaining the process or implementing a change to the process, based upon the determination of crude oil stability, wherein the controlling is changing a unit residence time.

2. The method of claim 1 wherein the linear correlation is established using the New Mexico Petroleum Recovery Research Center method designated as PRRC 01-18.

3. The method of claim 1 further comprising periodically determining the accuracy of the $SB_n$ determination using a turbidimetric flocculation titration method as a check on accuracy.

4. The method of claim 1 further comprising making an Asphaltene Stability Index determination for crude oil at or near the point of the refractive index probe location.

5. The method of claim 4 further comprising correlating the $SB_n$ determined using the refractive index probe with the ASI determination and using the correlated $SB_n$ in controlling the process.

6. A method of transporting or storing crude oil to mitigate asphaltene fouling comprising:
    deploying a refractive index probe in a crude oil transportation or storage system;
    making a measurement of crude oil stability by a process comprising a first part and a second part; wherein:
    the first part of the process is measuring RI parameters online using a refractive index probe;
    the second part of the process is converting the RI parameters into a "solubility blending number" (SBn) based on a linear correlation;
    the linear correlation is established using the New Mexico Petroleum Recovery Research Center method designated as PRRC 01-18; and
    then controlling the process for transporting or storing the crude oil by maintaining the process or implementing a change to the process, based upon the determination of crude oil stability, wherein the controlling is changing a unit residence time.

7. The method of claim 6 further comprising periodically determining the accuracy of the $SB_n$ determination using a turbidimetric flocculation titration method as a check on accuracy.

8. The method of claim 7 further comprising making an Asphaltene Stability Index determination for crude oil at or near the point of the refractive index probe location.

9. The method of claim 8 further comprising correlating $SB_n$ determined using the refractive index probe with the ASI determination.

10. The method of claim 9 further comprising using the correlated $SB_n$ to control the process to improve crude oil stability.

11. A method of monitoring the blending of two or more crude oil streams to form a combined feed stream to identify the stability of the two or more crude oil feed streams and to avoid asphaltene fouling by the combined feed stream comprising:
    employing a refractive index probe to measure at least the stability of the combined streams;
    wherein the measuring at least the stability is performed by a process comprising a first part and a second part;
    the first part of the process is measuring RI parameters online using a refractive index probe;
    the second part of the process is converting the RI parameters into a "solubility blending number" (SBn) based on a linear correlation; and the linear correlation is established using the New Mexico Petroleum Recovery Research Center method designated as PRRC 01-18;
    wherein the location of the refractive index probe is selected from the group consisting of: into a feed going into a desalting unit, into a heat exchanger, into a pre-heater, and combinations thereof;
    further comprising avoiding inducing asphaltene fouling using the SBn by implementing a change to the blending, based upon the determination of crude oil stability, by changing a unit residence time.

12. The method of claim 11 further comprising
    periodically determining the accuracy of the SBn determination using a turbidimetric flocculation titration method as a check on accuracy;
    making an Asphaltene Stability Index determination for crude oil at or near the point of the refractive index probe location; and correlating SBn determined using the refractive index probe with the ASI determination;

using the correlated SBn to adjusting the order of blending of feed streams to improve crude oil stability of a combined feed stream.

13. The method of claim 12 wherein the two or more crude oil streams are a heavy crude oil stream and a shale oil stream.

14. The method of claim 12 further comprising monitoring the Asphaltene Stability Index using only the RI data.

* * * * *